(12) United States Patent
Kurnik et al.

(10) Patent No.: US 8,265,879 B2
(45) Date of Patent: Sep. 11, 2012

(54) DETERMINATION OF SINGLE PEAK MELTING TEMPERATURE BY PCR ANALOGY AND DOUBLE SIGMOID EQUATION

(75) Inventors: Ronald T. Kurnik, Foster City, CA (US); Thomas Thurnherr, Lucerne (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 570 days.

(21) Appl. No.: 12/425,695

(22) Filed: Apr. 17, 2009

(65) Prior Publication Data

US 2010/0268472 A1    Oct. 21, 2010

(51) Int. Cl.
  *G01N 33/48* (2006.01)
(52) U.S. Cl. .......................................................... 702/19
(58) Field of Classification Search ...................... 702/19
  See application file for complete search history.

(56) References Cited

U.S. PATENT DOCUMENTS 6,303,305 B1   10/2001   Wittwer et al.

FOREIGN PATENT DOCUMENTS

EP          10003919          7/2010

OTHER PUBLICATIONS

Kirnik et al. (European patent application publication 06004794.1, date of publication: Sep. 13, 2006).*
Liu, Weihong, et al., 2002, "Validation of a quantitative method for real time PCR kinetics", Biochemical and Biophysical Research Communications, 294(2):347-353.
Mergny, Jean-Louis, et al., 2003, "Analysis of Thermal Melting Curves", Oligonucleotides, 13(6):515-537.
Pryor, Robert J., et al, 2006, "Real-Time Polymerase Chain Reaction and Melting Curve Analysis", Methods in Molecular Biology, 336:19-32.
Wilhelm, Jochen, et al., 2003, "SoFAR: Software for Fully Automatic Evaluation of Real-Time PCR Data", BioTechniques, 34(2):324-332.
Zhao, Sheng, et al., 2005, "Comprehensive Algorithm for Quantitative Real-Time Polymerase Chain Reaction", Journal of Computational Biology, 12(8):1047-1064.
U.S. Appl. No. 11/349,550, filed Feb. 6, 2006, Kurnik et al.

* cited by examiner

*Primary Examiner* — Jerry Lin
(74) *Attorney, Agent, or Firm* — Kilpatrick Townsend & Stockton LLP

(57) ABSTRACT

Systems and methods for determining melting temperatures, Tm, for DNA from melt curve data. The systems and methods also allow for quantitative determination of gene amount based on peak height. A PCR analogy is used to perform quantization of an acquired melting curve dataset. The melting curve is transformed using a horizontal flip and a horizontal translation, and a double sigmoid equation is then fit to the data. Inverse translation and inverse horizontal flip transforms are applied to the equation to produce an equation based solution of the melt curve dataset. The equation based solution of the melt curve is then used to determine the first derivative (e.g., Tm value) and peak height.

32 Claims, 9 Drawing Sheets

Figure 1: Fluorescence Intensity vs. Temperature

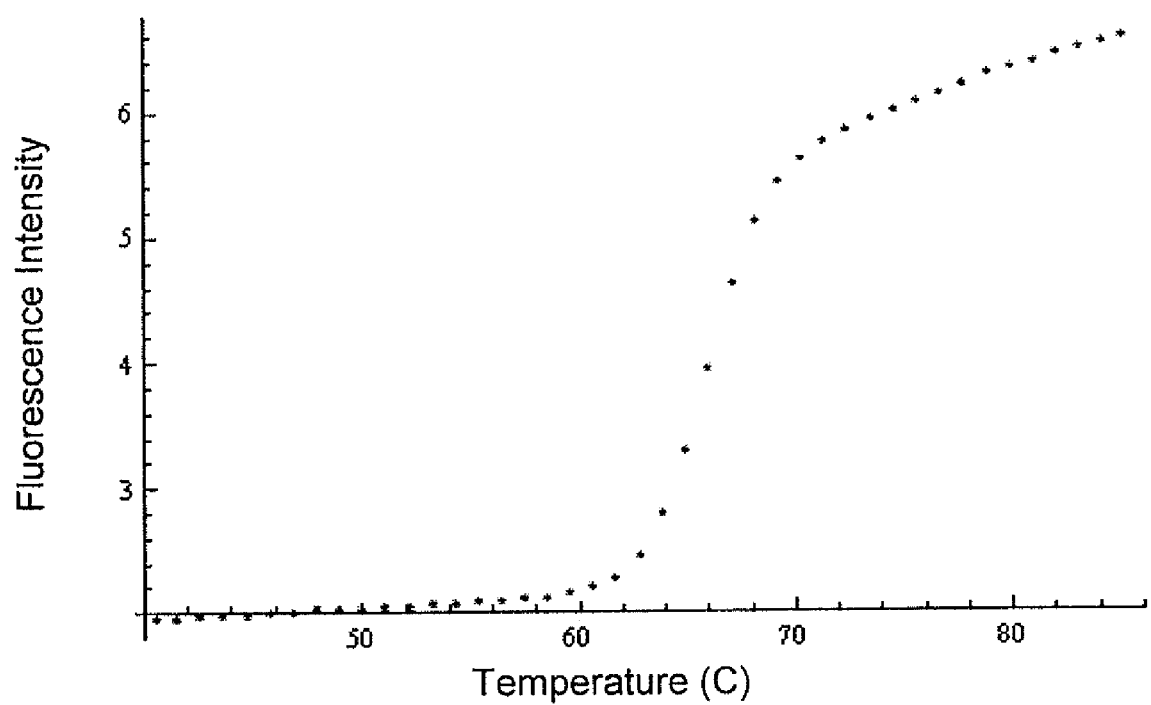
Figure 4: Raw Melt Curve after Horizontal Flip

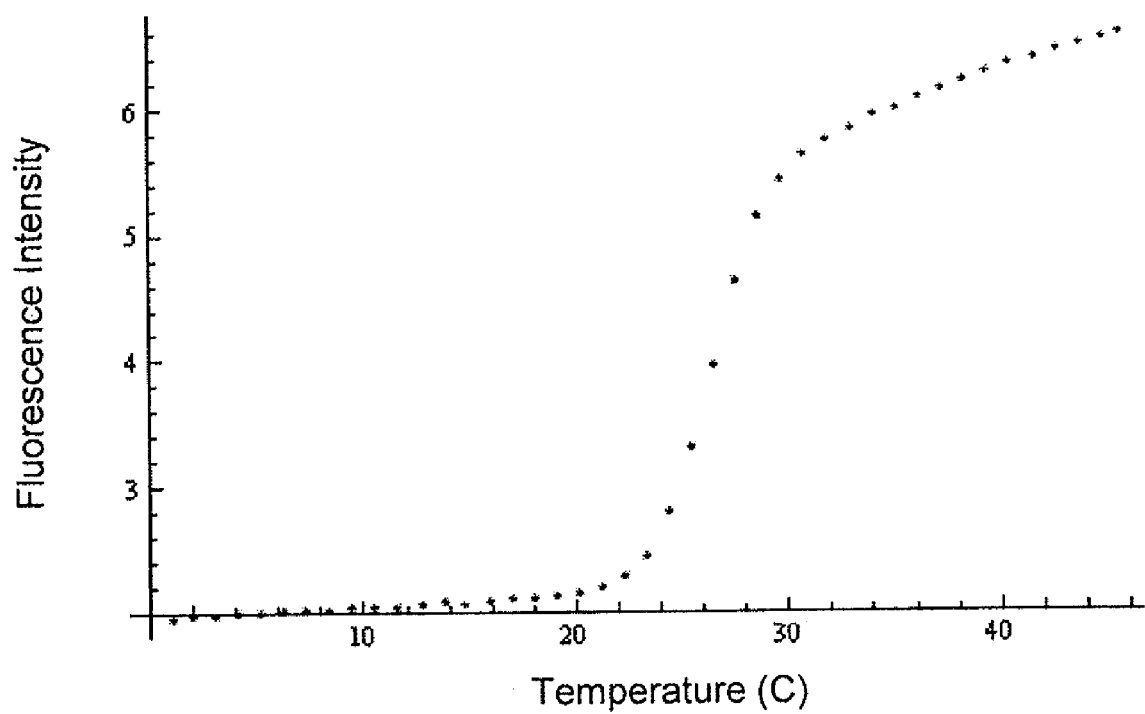
Figure 5: Translation of Melt Curve

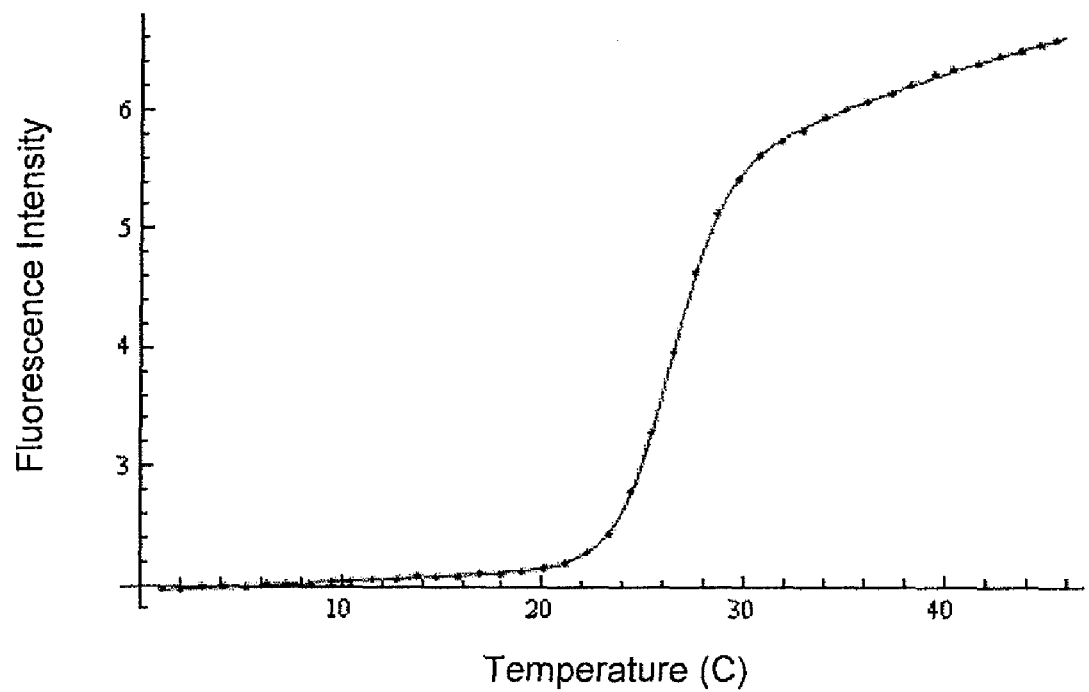
Figure 6: Regression of Double Sigmoid Equation to Figure 3

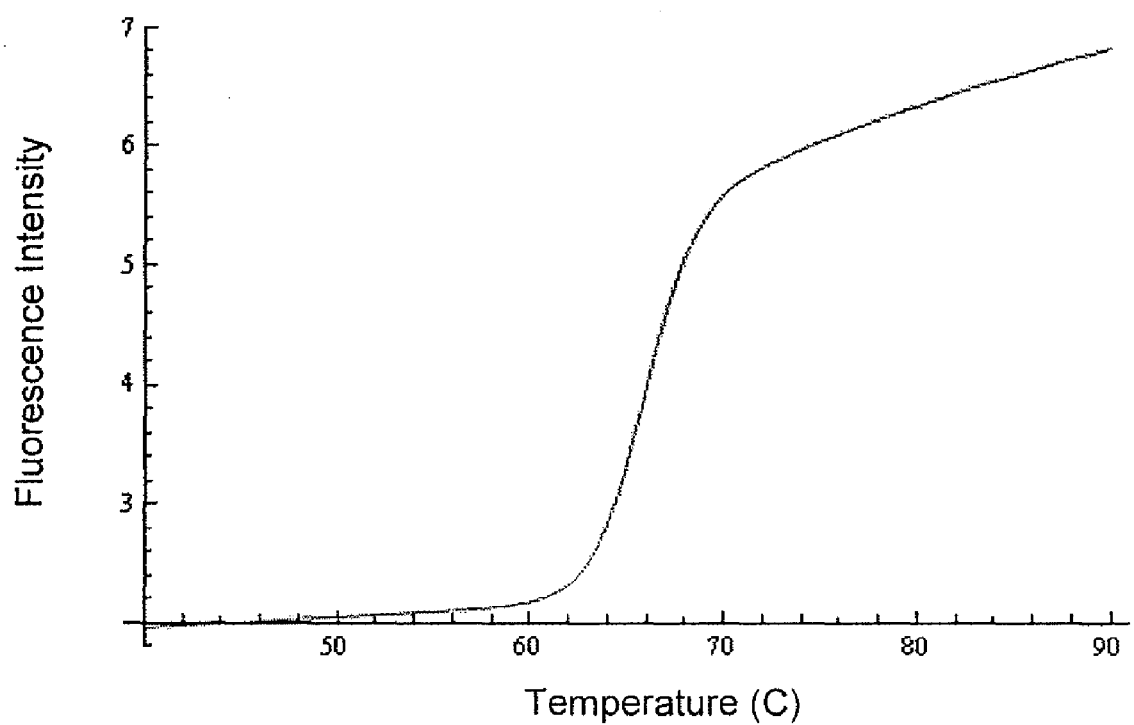
Figure 7: Inverse Translation of PCR-MELT Curve

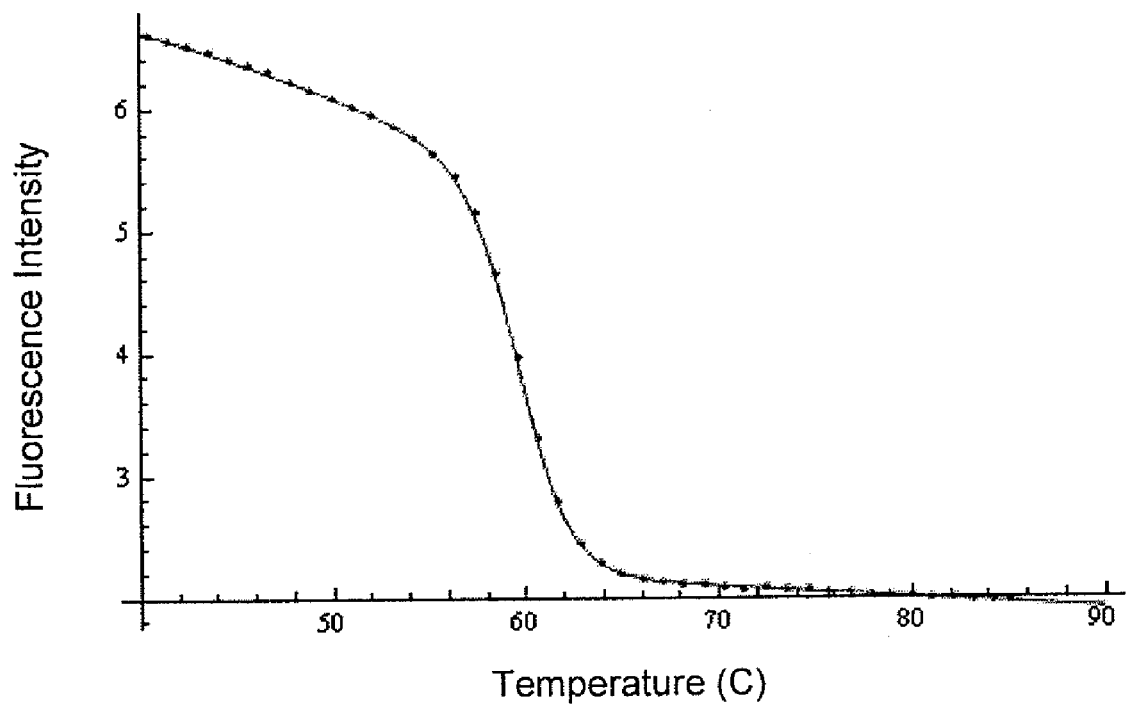
Figure 8: Melt Curve Established as PCR Curve

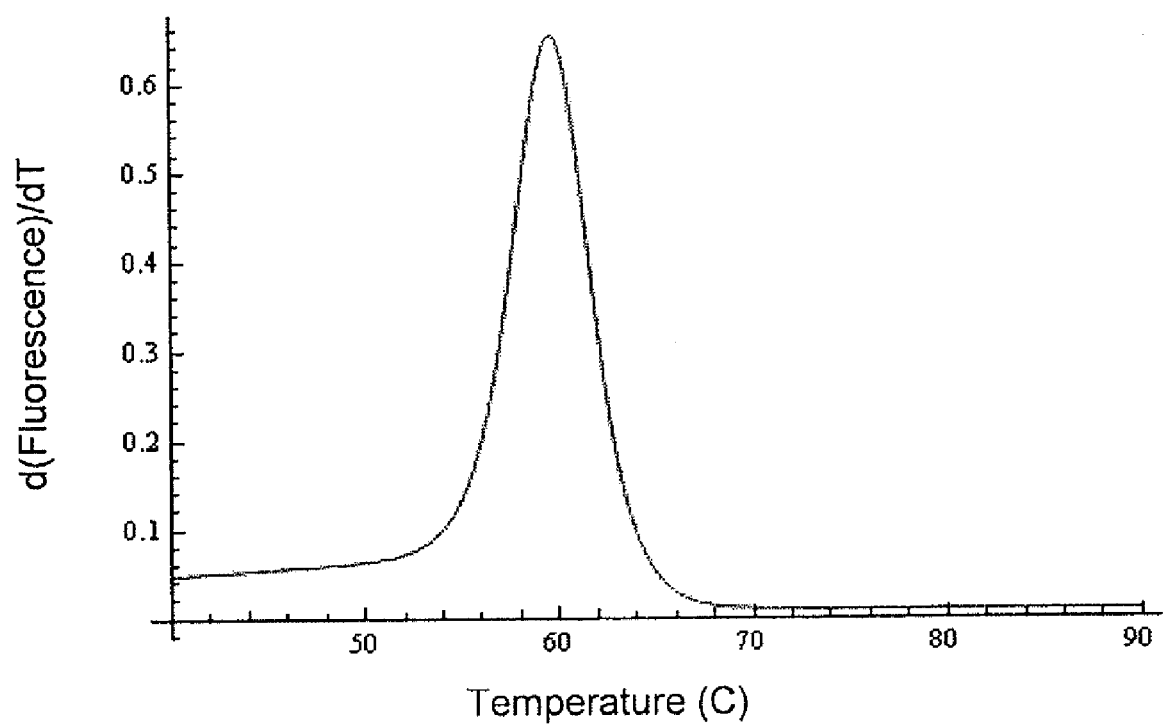
Figure 9: Derived Melt Peak Curve
DETERMINATION OF SINGLE PEAK MELTING TEMPERATURE BY PCR ANALOGY AND DOUBLE SIGMOID EQUATION

BACKGROUND

The present invention relates generally to processing data representing melt characteristics of oligonucleotides, and more particularly to systems and methods for determining melting temperatures for an oligonucleotide sample based on melt curve data.

Determination of oligonucleotide or DNA melting temperatures, usually performed directly after a PCR experiment, is an important method to distinguish genotypes. Some assays require the determination of multiple melting temperatures to identify wild-type from mutant genes. Alternatively, melting assays can be used with a single genotype to quantitatively determine the amount of a gene based on peak height. For example, recently discussed in the literature is the use of examining the KRAS gene to determine which patients might be candidates for a treatment for non-small cell lung cancer. Patients whose KRAS gene is of a wild-type would benefit from the treatment, whereas if the patient had a mutant variation of this gene, the treatment would be of no benefit. As these treatments often have major side effects, it is very important to determine the patient's correct genotype. It is also useful to know the amount of gene present.

Therefore, it is desirable to provide systems and methods that accurately and efficiently determine the melting temperature of a DNA sample and the amount of gene based on peak height.

BRIEF SUMMARY

The present invention provides systems and methods for determining the melting temperature, Tm, for oligonucleotides based on melt curve data. The systems and methods also allow for quantitative determination of the gene amount based on peak height.

According to various embodiments, a PCR analogy is used to perform quantization of an acquired melting curve dataset. In certain aspects, the melting curve is transformed using a horizontal flip and a horizontal translation. A double sigmoid equation is then fit to the data. Inverse translation and inverse horizontal flip transforms are then applied to the equation to produce an equation based solution of the melt curve dataset. The equation based solution of the melt curve is then used to determine the first derivative (e.g., Tm value) and peak height.

According to one aspect of the present invention, a computer-implemented method is provided for determining a melting temperature, Tm, of DNA. The method typically includes steps that are implemented in a processing module. The steps of the method typically include receiving a dataset representing a melt curve for a DNA sample, the dataset including a plurality of data points represented as a sequence of data values $\{(X_1,Y_1), (X_2,Y_2) \ldots (X_{n-1},Y_{n-1}), (X_n,Y_n)\}$, where X represents a temperature (T) value and Y represents a fluorescence intensity value, determining an analytical expression that fits the dataset, and determining a derivative curve by taking the derivative of the analytical expression with respect to X. The steps of the method also typically include determining a value $X_{max}$ corresponding to a maximum derivative (dY/dX) value of the derivative curve, and outputting the value $X_{max}$, wherein the value $X_{max}$ represents a melting temperature, $T_m$, of the DNA sample. In certain aspects, the method further includes determining the peak height of the derivative curve corresponding to the $T_m$ value, and outputting the peak height. In certain aspects, the analytical expression is determined by calculating an approximation of a curve that fits the dataset by applying a regression process to a double sigmoid function to determine parameters of the function. In certain aspects, the regression process is a Levenberg-Marquardt regression process.

According to another aspect of the present invention, a computer readable medium including code for controlling a processor to determining a melting temperature, Tm, of DNA is provided. The code typically includes instructions to receive a dataset representing a melt curve for a DNA sample, the dataset including a plurality of data points represented as a sequence of data values $\{(X_1,Y_1), (X_2,Y_2) \ldots (X_{n-1},Y_{n-1}), (X_n,Y_n)\}$, where X represents a temperature (T) value and Y represents a fluorescence intensity value, instructions to determine an analytical expression that fits the dataset, and instructions to determine a derivative curve by taking the derivative of the analytical expression with respect to X. The code also typically includes instructions to determine a value $X_{max}$ corresponding to a maximum derivative (dY/dX) value of the derivative curve, and instructions to output the value $X_{max}$, wherein the value $X_{max}$ represents a melting temperature, $T_m$, of the DNA sample. In certain aspects, the code further includes instructions to determine the peak height of the derivative curve corresponding to the $T_m$ value, and output the peak height. In certain aspect, the analytical expression is determined by calculating an approximation of a curve that fits the dataset by applying a regression process to a double sigmoid function to determine parameters of the function. In certain aspects, the regression process is a Levenberg-Marquardt regression process.

According to yet another aspect of the present invention, a kinetic Polymerase Chain Reaction (PCR) system is provided. The PCR system typically includes a kinetic PCR analysis module that generates a melt curve dataset representing a DNA melt curve, the dataset including a plurality of data points represented as a sequence of data values $\{(X_1,Y_1), (X_2,Y_2) \ldots (X_{n-1},Y_{n-1}), (X_n,Y_n)\}$, where X represents a temperature (T) value and Y represents a fluorescence intensity value, and an intelligence module adapted to process the melt curve dataset to determine a Tm value. The Intelligence module is typically adapted to determine a Tm value by determining an analytical expression that fits the dataset, to determine a derivative curve by taking the derivative of the analytical expression with respect to X, and to determine a value Xmax corresponding to a maximum derivative (dY/dX) value of the derivative curve. The Intelligence module is further typically adapted to output the value Xmax, wherein the value $X_{max}$ represents a melting temperature, Tm, of the DNA sample. In certain aspects, the intelligence module includes one or more processors.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 4 illustrates the results of a horizontal flip transform applied to the data set of FIG. 1.

FIG. 5 illustrates the results of a horizontal translation transform applied to the data set of FIG. 4.

FIG. 6 illustrates a resultant double sigmoid curve fit to the data in FIG. 5.

FIG. 7 illustrates a result of the inverse translation transform.

FIG. 8 illustrates a melt curve established as a PCR curve.

FIG. 9 illustrates a graphical representation of a derived melt peak curve.

DETAILED DESCRIPTION

The present invention provides systems and methods for determining melting temperatures, Tm, for DNA from melt curve data. The systems and methods also allow for quantitative determination of gene amount based on peak height.

Figure 1:
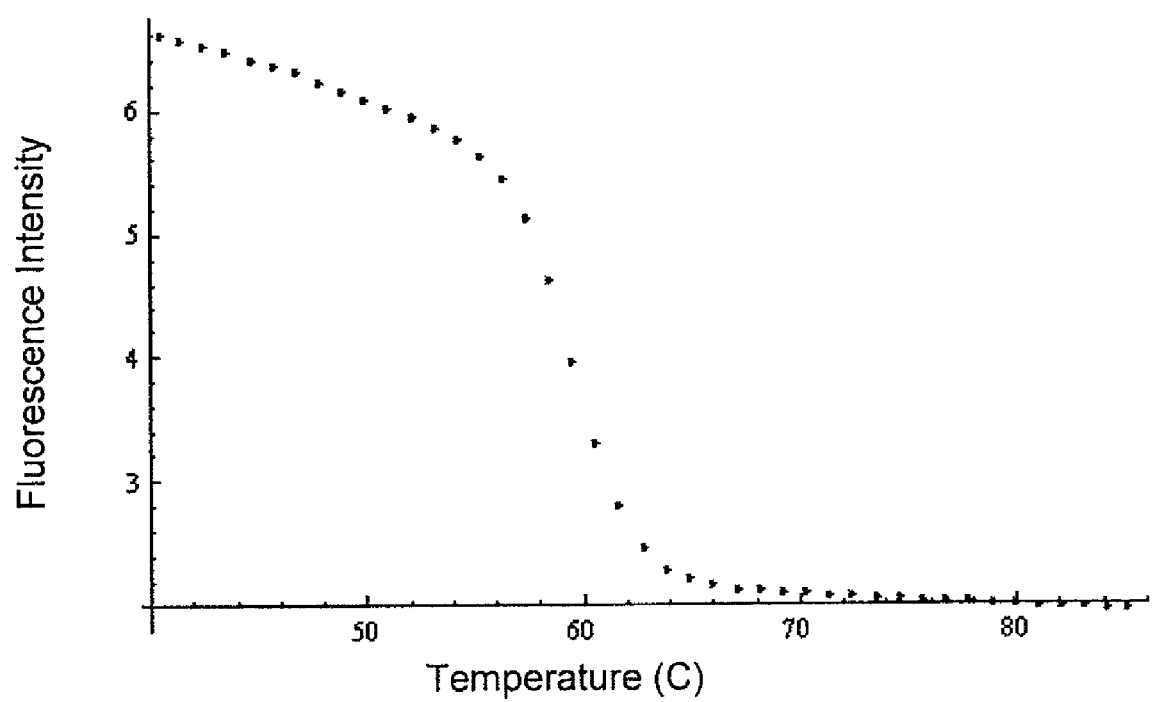
FIG. 1 illustrates an example of a melt curve in the context of a PCR process.

One example of a melt curve in the context of a PCR process is shown in FIG. 1. The curve shown in FIG. 1 is a typical melting curve graph that was generated after a PCR experiment in the case where there is only one genotype present. In this curve, the fluorescence intensity decreases as a function of increasing temperature.

As shown in FIG. 1, data for a typical melt curve can be represented in a two-dimensional coordinate system, for example, with temperature defining the x-axis and an indicator of accumulated polynucleotide defining the y-axis. Typically, the indicator of accumulated polynucleotide is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance.

General Process Overview

Figure 2:
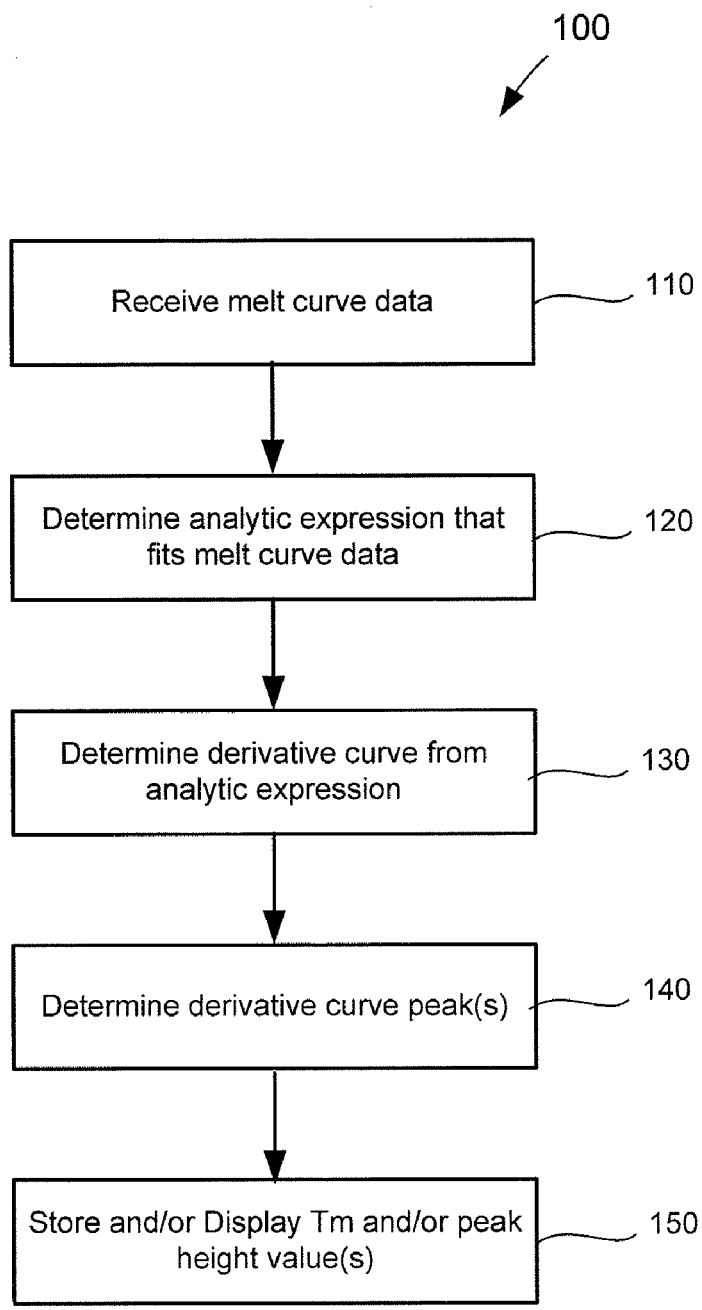
FIG. 2 illustrates a process for determining a melting temperature according to one embodiment.

Consider a typical melt curve as shown in FIG. 1. It is desired to obtain one or more melting temperatures from the data represented in FIG. 1. According to one embodiment, a process 100 for determining a melting temperature can be described briefly with reference to FIG. 2. In step 110, an experimental data set representing the melt curve is received or otherwise acquired. An example of a plotted melt curve data set is shown in FIG. 1, where the y-axis (abscissa) and x-axis (ordinate) represent fluorescence intensity and temperature, respectively, for a melt curve. The acquired dataset includes a plurality of data points represented as a sequence of data values $\{(X_1,Y_1), (X_2,Y_2) \ldots (X_{n-1},Y_{n-1}), (X_n,Y_n)\}$, where X represents a temperature (T) value and Y represents a fluorescence intensity value. In certain aspects, the data set should include data that is continuous and equally spaced along the ordinate axis.

In the case where process 100 is implemented in an intelligence module (e.g., one or more processors executing instructions) resident in a PCR device such as a thermocycler, the data set may be provided to the intelligence module in real time as the data is being collected, or it may be stored in a memory unit or buffer and provided to the intelligence module after an experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection), to the acquiring device, or provided on a portable medium such as a CD, DVD, floppy disk or the like. In certain aspects, the data set includes data points having a pair of coordinate values (or a 2-dimensional vector). For melt data, the pair of coordinate values typically represents the temperature and the fluorescence intensity value. When displayed in a two-dimensional graph, for example, the x-axis (ordinate) typically represents the temperature and the y-axis (abscissa) typically represents the fluorescence intensity. After the data set has been received or acquired in step 110, the data set may be analyzed to determine the melting temperature(s) and/or peak height values of derivative curves.

In step 120, an analytical expression that fits the dataset is determined. As will be discussed in more detail later, in certain aspects, a double sigmoid type equation is fit to the data set. In certain aspects, a Levenberg-Marquardt regression process is used to fit the double sigmoid equation to the data set, although other regression processes may be used. In step 130, a derivative curve is determined from the analytic expression by taking the derivative of the analytical expression with respect to X (temperature). A peak in the derivative curve is then determined in step 140 by determining a value Xmax corresponding to a maximum derivative (dY/dX) value of the derivative curve. In certain aspects, standard analytical methods of curve maximization, such as Newton, Gradient, Grid Search, and other methods, are used to determine maximum value(s) Xmax of the derivative curve. A value Xmax represents a melting temperature, Tm, of the DNA sample. In step 150, the Tm value(s) and/or peak height value(s) are returned, e.g., for display or further processing. Graphical displays may be rendered with a display device, such as a monitor screen or printer, coupled with the system that performed the analysis of FIG. 2, or data may be provided to a separate system for rendering on a display device.

Figure 3:
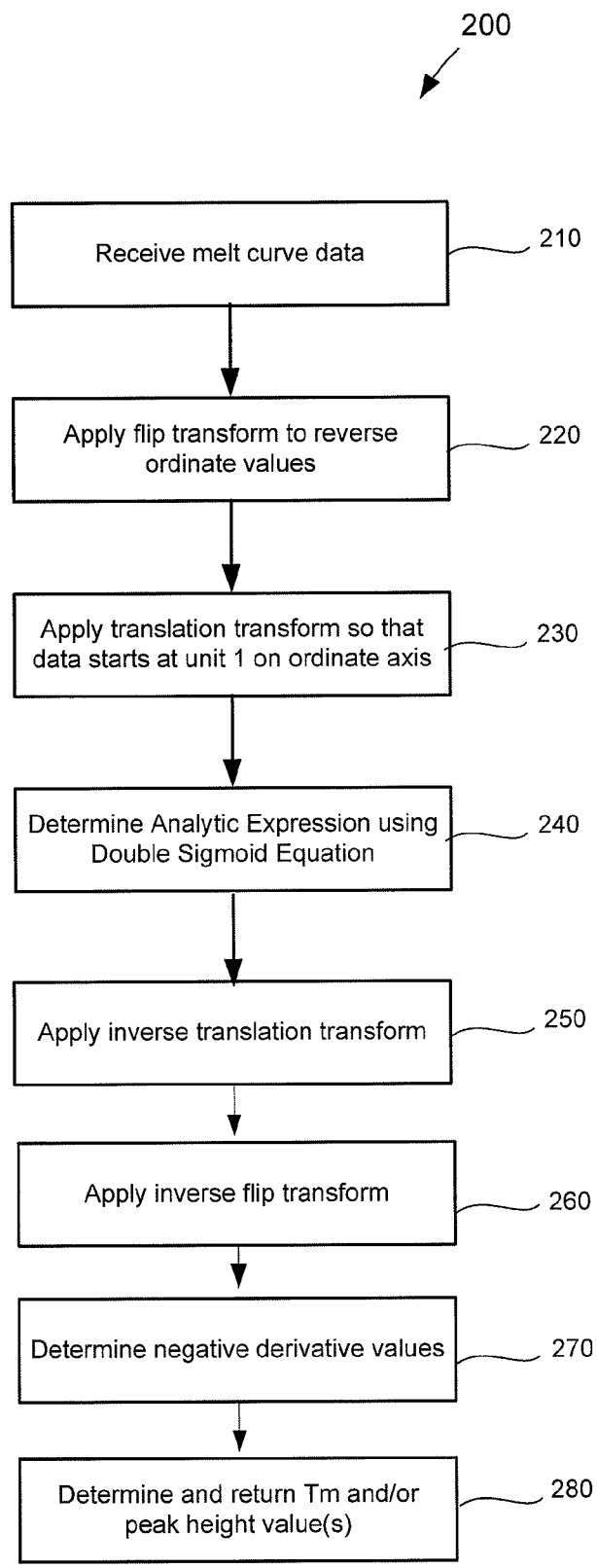
FIG. 3 illustrates a process for determining a melting temperature using a PCR analogy according to one embodiment.

FIG. 3 illustrates a process 200 of determining a melting temperature using a PCR analogy according to one embodiment. In this embodiment, the melt curve dataset is transformed to be similar to that of a PCR curve (e.g., when visually viewing the dataset) so as to take advantage of previous algorithms designed to process and analyze PCR data, and hence to determine an analytic equation that fits the melt curve dataset.

In step 210, the melt curve data set is received or otherwise acquired as in step 110. In step 220 through 260, an analytical expression that fits the dataset is determined. In step 220, according to one embodiment, a horizontal flip transform is applied to the data set so that the temperature values are reversed. For example, a transform is applied such that a sequence $\{\{T_1,F_1\}, \{T_2,F_2\}, \ldots, \{T_{n-1},F_{n-1}\}, \{T_n,F_n\}\}$ would become $\{\{T_n,F_1\}, \{T_{n-1},F_2\}, \ldots, \{T_2,F_{n-1}\},\{T_1,F_n\}\}$, where T represents temperature, F represents fluorescence, and the subscript represents order in a sequence. Performing this transformation on the data in FIG. 1 yields the result shown in FIG. 4. As FIG. 4 indicates, this shape is now representative of a typical PCR curve. In step 230, a horizontal translation transform is applied to the data set so that the dataset starts at unit 1 (e.g., 1 degree Celsius) on the X-axis. In this manner, the curve is shifted to the left, so that it starts at 1° C. in order to have identical characteristics of a PCR curve, so that analytical expressions previously developed for PCR can be readily applied to the melt curve. The result of this translation to the data of FIG. 4 (in this case by 39.47 C.) is shown in FIG. 5. It should be appreciated that steps 230 need not be performed, and that the order of steps 220 and 230 may be reversed.

In step 240, an analytic equation is fit to the data of FIG. 5. In one embodiment, a double sigmoid equation is fit to the data curve. As the curve in FIG. 5 has the characteristics of a PCR curve, methods previously developed to fit a double sigmoid equation can be applied to this data. In step 240, in one embodiment, a double sigmoid function with parameters determined by a Levenberg-Marquardt (LM) regression process or other regression process is used to find an approximation of a curve representing the data set. The LM method is a non-linear regression process; it is an iterative technique that minimizes the square of the distance between a non-linear function and a data set. The process behaves like a combination of a steepest descent process and a Gauss-Newton process: when the current approximation doesn't fit well it behaves like the steepest descent process (slower but more reliable convergence), but as the current approximation becomes more accurate it will then behave like the Gauss-Newton process (faster but less reliable convergence). The LM regression method is widely used to solve non-linear regression problems.

In general, the LM regression method includes an algorithm that requires various inputs and provides output. In one aspect, the inputs include a data set to be processed, a function that is used to fit the data, and an initial guess for the parameters or variables of the function. The output includes a set of parameters for the function that minimizes the distance between the function and the data set.

According to one embodiment, the fit function is a double sigmoid of the form:

$$f(x) = a + bx + \frac{c}{(1 + \exp^{-d(x-e)})(1 + \exp^{-f(x-g)})}. \quad (1)$$

The choice of this equation as the fit function is based on its flexibility and its ability to fit the different curve shapes that a typical PCR curve or other growth curve may take. One skilled in the art will appreciate that variations of the above fit function or other fit functions may be used as desired. The double sigmoid equation (1) has 7 parameters: a, b, c, d, e, f and g. The equation can be decomposed into a sum of a constant, a slope and a double sigmoid. The double sigmoid itself is the multiplication of two sigmoids. Details on methods to fit a double sigmoid equation to a PCR data set, including parameter determination, can be found in U.S. application Ser. No. 11/349,550, filed Feb. 6, 2006, which is hereby incorporated by reference in its entirety.

The resultant double sigmoid curve fit to the data in FIG. 5 is shown in FIG. 6, and the double sigmoid expression is shown in Equation 2:

$$ds(x) = 1.94755 + 0.00905407x + \frac{5.14876}{(1+e^{-0.755673(-26.2596+x)})(1+e^{-0.0529859(-16.2445+x)})} \quad (2)$$

The double sigmoid expression in Equation 2 has to now be transformed back into the raw melt curve format. In step 250, the curves and double sigmoid expression corresponding to FIG. 6 and equation 2 are shifted by the negative amount shifted in step 230. The resultant shifted curve and double sigmoid expression are shown in FIG. 7 and Equation 3 respectively $$ds2(x) = 1.94755 + 0.00905407(-39.47 + x) + \frac{5.14876}{(1+e^{-0.755673(-65.7296+x)})(1+e^{-0.0529859(-55.7145+x)})} \quad (3)$$

In step 260, a function for inverse horizontal flip of the curve shown in FIG. 7 is determined and applied. The function for inverse horizontal flip can be determined as the sum of the first and last x-axis coordinates of the original raw melt curve minus x. For example, assume the original raw melt data is $\{\{T_1,F_1\}, \{T_2,F_2\}, \ldots, \{T_{n-1},F_{n-1}\}, \{T_n,F_n\}\}$. Then the inverse horizontal flip function is: $(T_1+T_n)-x$. For the data in FIG. 7, the inverse function is found to be InvFlip(x)=125-x.

The re-establishment of the original melt function and curve are shown in FIG. 8 and Equation 4:

$$ds3(x) = ds2(InvFlip(x)) = 1.94755 + 0.00905407(86.03 - x) + \frac{5.14876}{(1+e^{-0.755673(59.7704-x)})(1+e^{-0.0529859(69.7855-x)})}$$

Equation 4 is determined as ds3(x)=ds2(InvFlip(x)). The graph of ds3(x) with superposition of the original raw melt data is shown in FIG. 8. It is seen that the fit is near perfect, thereby establishing the functional equivalence between a raw melt curve and a PCR curve.

In step 270, the negative derivative of the functional form of the raw melt curve is determined; the representation of the peaks for melting are established by taking the negative derivative of the raw melt data. Using the equivalent analytical expression for the raw melt curve, the expression of the melt peak curve is derived as Equation 5:

$$\text{melt peak curve} = -\frac{d(ds3(x))}{dx} \quad (5)$$

The graphical representation of Equation 5 is shown in FIG. 9.

In step 280, the melting temperature, Tm, and/or the peak height are determined and returned, e.g., for display or further processing. The melting temperature is determined as the temperature corresponding to the maximum of the melt peak curve. The melting temperature, Tm, can be found by standard analytical methods of curve maximization, such as Newton, Gradient, Grid Search, and other methods. In the example used herein, the maximum temperature was found to be Tm=59.64, and the peak height is found to be peak height=0.655.

The methodologies described herein can be extended to melting curves with multiple peaks by using an analytical expression for a PCR curve that allows for multiple elbows. Alternatively, one can re-establish procedures to directly apply a double sigmoid expression to the original raw melt curve, so that the melt-PCR analogy is not required. Details for establishing such procedures can be found in U.S. application Ser. No. 11/349,550, filed Feb. 6, 2006, which has been hereby incorporated by reference in its entirety.

It should be appreciated that the Tm determination processes may be implemented in computer code running on a processor of a computer system. The code includes instructions for controlling a processor to implement various aspects and steps of the Tm determination processes. The code is typically stored on a hard disk, RAM or portable medium such as a CD, DVD, etc. Similarly, the processes may be implemented in a PCR device such as a thermocycler, or other specialized device, including a processor executing instructions stored in a memory unit coupled to the processor. Code including such instructions may be downloaded to the device memory unit over a network connection or direct connection to a code source or using a portable medium as is well known.

One skilled in the art should appreciate that the Tm determination processes of the present invention can be coded using a variety of programming languages such as C, C++, C#, Fortran, VisualBasic, etc., as well as applications such as Mathematica® which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A computer-implemented method of determining a melting temperature, Tm, of DNA, the method comprising:
   receiving a dataset representing a melt curve for a DNA sample, the dataset including a plurality of data points represented as a sequence of data values $\{(X_1,Y_1), (X_2,Y_2) \ldots (X_{n-1},Y_{n-1}), (X_n,Y_n)\}$, where X represents a temperature (T) value and Y represents a fluorescence intensity value;
   determining, with a computer system comprising a processor, an analytical expression that fits the dataset, wherein the analytical expression is determined by:
      calculating an approximation of a curve that fits the dataset by applying a regression process to a double sigmoid function to determine parameters of the double sigmoid function, the double sigmoid function having the form:

$$a + bx + \frac{c}{(1 + \exp^{-d(x-e)})(1 + \exp^{-f(x-g)})},$$

where a, b, c, d, e, f, and g are the parameters;
   determining a derivative curve by taking the derivative of the analytical expression with respect to X;
   determining a value $X_{max}$ corresponding to a maximum derivative (dY/dX) value of the derivative curve; and
   outputting the value $X_{max}$, wherein the value $X_{max}$ represents a melting temperature, $T_m$, of the DNA sample.

2. The method of claim 1, further including:
   determining the peak height of the derivative curve corresponding to the $T_m$ value; and
   outputting the peak height.

3. The method of claim 1, wherein the regression process is a Levenberg-Marquardt regression process.

4. The method of claim 1, wherein the analytical expression is determined by:
   applying a first transform to the dataset such that the sequence of data values $\{(X_1,Y_1), (X_2,Y_2) \ldots (X_{n-1},Y_{n-1}), (X_n,Y_n)\}$ becomes a transformed sequence $\{(X_n,Y_1), (X_{n-1},Y_2) \ldots (X_2,Y_{n-1}), (X_{1n},Y_n)\}$,
   wherein calculating an approximation of a curve that fits the dataset includes:
      calculating an approximation of a curve that fits the transformed sequence by applying a regression process to the double sigmoid function to determine the parameters of the double sigmoid function.

5. The method of claim 4, wherein the regression process is a Levenberg-Marquardt regression process.

6. The method of claim 4, further including applying a second transform to the double sigmoid function, the second transform being inverse to the first transform.

7. The method of claim 6, wherein the second transform includes a function of the form $(X_1+X_n)-x$.

8. The method of claim 4, further including, prior to calculating:
   shifting the X values of the dataset or of the transformed sequence by a first amount ($X_{trans}$) so that the transformed sequence begins at a value of 1 unit.

9. The method of claim 8, further including, after calculating, shifting the X values of the double sigmoid function by $-X_{trans}$.

10. The method of claim 1, wherein determining a derivative curve includes taking the negative derivative of the analytical expression with respect to X.

11. The method of claim 1, wherein the computer system is integrated with a PCR data acquiring device or system.

12. A non-transitory computer readable medium including code for controlling a processor to determine a melting temperature, Tm, of DNA, the code including instructions to:
   receive a dataset representing a melt curve for a DNA sample, the dataset including a plurality of data points represented as a sequence of data values $\{(X_1,Y_1), (X_2,Y_2) \ldots (X_{n-1},Y_{n-1}), (X_n,Y_n)\}$, where X represents a temperature (T) value and Y represents a fluorescence intensity value;
   determine an analytical expression that fits the dataset, wherein the analytical expression is determined by:
      calculating an approximation of a curve that fits the dataset by applying a regression process to a double sigmoid function to determine parameters of the double sigmoid function, the double sigmoid function having the form:

$$a + bx + \frac{c}{(1 + \exp^{-d(x-e)})(1 + \exp^{-f(x-g)})},$$

where a, b, c, d, e, f, and g are the parameters;
   determine a derivative curve by taking the derivative of the analytical expression with respect to X;
   determine a value $X_{max}$ corresponding to a maximum dY/dX value of the derivative curve; and
   output the value $X_{max}$, wherein the value $X_{max}$ represents a melting temperature, $T_m$, of the DNA sample.

13. The computer readable medium of claim 12, further including instructions to:
   determine the peak height of the derivative curve corresponding to the $T_m$ value; and
   output the peak height.

14. The computer readable medium of claim 12, wherein the regression process is a Levenberg-Marquardt regression process.

15. The computer readable medium of claim 12, wherein the instructions to determine the analytical expression includes instructions to:

apply a first transform to the dataset such that the sequence of data values $\{(X_1,Y_1), (X_2,Y_2) \ldots (X_{n-1},Y_{n-1}), (X_n,Y_n)\}$ becomes a transformed sequence $\{(X_n,Y_1), (X_{n-1},Y_2) \ldots (X_2,Y_{n-1}), (X_1,Y_n)\}$, wherein calculating an approximation of a curve that fits the dataset includes:

calculating an approximation of a curve that fits the transformed sequence by applying a regression process to the double sigmoid function to determine the parameters of the double sigmoid function.

16. The computer readable medium of claim 15, wherein the regression process is a Levenberg-Marquardt regression process.

17. The computer readable medium of claim 15, further including instructions to apply a second transform to the double sigmoid function, the second transform being inverse to the first transform.

18. The computer readable medium of claim 17, wherein the second transform includes a function of the form $(X_1 + X_n) - x$.

19. The computer readable medium of claim 15, further including instructions to shift the X values of the dataset or of the transformed sequence by a first amount $(X_{trans})$ before calculating so that the transformed sequence begins at a value of 1 unit.

20. The computer readable medium of claim 19, further including instructions to, after calculating, shift the X values of the double sigmoid function by $-X_{trans}$.

21. The computer readable medium of claim 12, wherein determining a derivative curve includes taking the negative derivative of the analytical expression with respect to X.

22. The computer readable medium of claim 12, wherein the processor is integrated in one of a computer system or a PCR data acquiring device or system.

23. A kinetic Polymerase Chain Reaction (PCR) system, comprising:

a kinetic PCR analysis module that generates a melt curve dataset representing a DNA melt curve, said dataset including a plurality of data points represented as a sequence of data values $\{(X_1,Y_1), (X_2,Y_2) \ldots (X_{n-1}, Y_{n-1}), (X_n,Y_n)\}$, where X represents a temperature (T) value and Y represents a fluorescence intensity value; and a processor adapted to process the melt curve dataset to determine a Tm value, by:

determining, with a computer system comprising a processor, an analytical expression that fits the dataset, wherein the analytical expression is determined by:

calculating an approximation of a curve that fits the dataset by applying a regression process to a double sigmoid function to determine parameters of the double sigmoid function, the double sigmoid function having the form:

$$a + bx + \frac{c}{(1 + \exp^{-d(x-e)})(1 + \exp^{-f(x-g)})},$$

where a, b, c, d, e, f, and g are the parameters;

determining a derivative curve by taking the derivative of the analytical expression with respect to X;

determining a value Xmax corresponding to a maximum derivative (dY/dX) value of the derivative curve; and outputting the value Xmax, wherein the value Xmax represents a melting temperature, Tm, of the DNA sample.

24. The kinetic PCR system of claim 23, wherein the processor is further adapted to:

determine the peak height of the derivative curve corresponding to the $T_m$ value; and output the peak height.

25. The kinetic PCR system of claim 23, wherein the regression process is a Levenberg-Marquardt regression process.

26. The kinetic PCR system of claim 23, wherein the analytical expression is determined by:

applying a first transform to the dataset such that the sequence of data values $\{(X_1,Y_1), (X_2,Y_2) \ldots (X_{n-1}, Y_{n-1}), (X_n,Y_n)\}$ becomes a transformed sequence $\{(X_n, Y_1), (X_{n-1},Y_2) \ldots (X_2,Y_{n-1}), (X_1,Y_n)\}$, wherein calculating an approximation of a curve that fits the dataset includes:

calculating an approximation of a curve that fits the transformed sequence by applying a regression process to the double sigmoid function to determine the parameters of the double sigmoid function.

27. The kinetic PCR system of claim 26, wherein the regression process is a Levenberg-Marquardt regression process.

28. The kinetic PCR system of claim 26, wherein the analytical expression is further determined by applying a second transform to the double sigmoid function, the second transform being inverse to the first transform.

29. The kinetic PCR system of claim 28, wherein the second transform includes a function of the form $(X_1+X_n)-x$.

30. The kinetic PCR system of claim 26 wherein the processor is further adapted to, prior to calculating, shift the X values of the dataset or of the transformed sequence by a first amount $(X_{trans})$ so that the transformed sequence begins at a value of 1 unit.

31. The kinetic PCR system of claim 30, wherein the processor is further adapted to, after calculating, shift the X values of the double sigmoid function by $-X_{trans}$.

32. The kinetic PCR system of claim 23, wherein determining a derivative curve includes taking the negative derivative of the analytical expression with respect to X.

* * * * *